United States Patent [19]

Grollier

[11] Patent Number: 4,736,756

[45] Date of Patent: Apr. 12, 1988

[54] COSMETIC COMPOSITIONS BASED ON NONIONIC, WEAKLY ANIONIC OR AMPHOTERIC SURFACE-ACTIVE AGENTS AND ON HETEROPOLY-SACCHARIDES

[75] Inventor: Jean F. Grollier, Paris, France

[73] Assignee: L'Oreal, Paris, France

[21] Appl. No.: 777,349

[22] Filed: Sep. 18, 1985

[30] Foreign Application Priority Data

Sep. 21, 1984 [LU] Luxembourg ............................ 85546
Sep. 21, 1984 [LU] Luxembourg ............................ 85547
Sep. 21, 1984 [LU] Luxembourg ............................ 85548

[51] Int. Cl.$^4$ .......................... A45D 7/00; A61K 7/06
[52] U.S. Cl. ................. 132/7; 424/DIG. 4; 424/70
[58] Field of Search .......... 424/70, DIG. 4; 514/777; 536/123; 132/7

[56] References Cited

U.S. PATENT DOCUMENTS

| | | | |
|---|---|---|---|
| 3,894,976 | 7/1975 | Kang et al. | 536/123 |
| 4,270,916 | 6/1981 | Racciato | 8/527 |
| 4,401,760 | 8/1983 | Peik et al. | 536/123 |
| 4,575,551 | 3/1986 | Fujiyama et al. | 536/123 |

FOREIGN PATENT DOCUMENTS

| | | | |
|---|---|---|---|
| 0111895 | 6/1984 | European Pat. Off. | 514/847 |
| 0113418 | 7/1984 | European Pat. Off. | 424/70 |
| 2531093 | 2/1984 | France | 424/70 |
| 59-605 | 4/1984 | Japan | 514/844 |
| 7104188 | 10/1972 | Netherlands | 424/70 |
| 1604859 | 12/1981 | United Kingdom | 424/70 |
| 2136689 | 9/1984 | United Kingdom | 424/70 |
| 2142348 | 1/1985 | United Kingdom | 8/406 |

OTHER PUBLICATIONS

Cosmetics & Toiletries, vol. 99, Feb. 1984, "The Structure of Amphoterics Derived from Imidazoline", Rieger, pp. 61, 63, 65.

Primary Examiner—Dale R. Ore
Attorney, Agent, or Firm—Cushman, Darby & Cushman

[57] ABSTRACT

The invention relates to a cosmetic composition for hair containing, in a cosmetically acceptable medium, at least:

(a) a water-soluble polyglycerolated nonionic surface agent, or
(b) a weakly anionic surface-active agent from the group of polyalkoxycarboxylates, or
(c) an amphoteric surface-active agent from the group of the acylated derivatives of mono- or dicarboxylic, optionally cyclic, diamino acids, or
(d) their mixtures, and at least one water-soluble heteropolysaccharide.

24 Claims, No Drawings

COSMETIC COMPOSITIONS BASED ON NONIONIC, WEAKLY ANIONIC OR AMPHOTERIC SURFACE-ACTIVE AGENTS AND ON HETEROPOLY-SACCHARIDES

The present invention relates to cosmetic compositions intended particularly to be applied on hair, based on surfactants and heteropolysaccharides.

Cosmetic compositions such as, more particularly, shampoos containing nonionic, weakly anionic or amphoteric surfactants are well known in the field of cosmetics and offer many advantages when compared to the compositions containing strongly anionic surfactants and have, in particular, a better skin tolerance.

"Weakly anionic surfactants" means surfactants incorporating, in their hydrophilic chain, a carboxylic acid function and other hydrosolubilizing groups which endow it with a significant solubility in water in an acidic medium; in such a medium, they show a behaviour which is similar to that of nonionic surfactants. The hydrosolubilizing groups are generally "polyethoxy" concatenations.

Nonionic surface-active agents which are especially interesting because of their compatibility with the scalp and with hair, and chiefly for persons with seborrhea problems, are water-soluble polyglocerolated surface-active agents, and particularly the condensation products of a monoalcohol, an α-diol, an alkylphenol, an amide or a diglycolamide with glycidol or a glycidol precursor, which are described in French Pat. No. 2,091,516, the compounds described in French Pat. No. 1,477,048 and the compounds described in French Pat. No. 2,328,763.

Weakly anionic surface-active agents which are of interest belong to the group of polyalkoxycarboxylates and amphoteric surface-active agents are chosen from the acylated derivatives of mono- or dicarboxylic diaminoacids present, when appropriate, in their cyclic form.

The use of surfactants of this type in a liquid form is not easy because the product is difficult to localize on hair and quickly flows towards the ends.

Furthermore, it has been found difficult to thicken the compositions based on these surface-active agents with traditional thickeners such as cellulose derivatives, crosslinked acrylic acid polymers, guar gum derivatives, or polyethylene glycol esters, either because the solutions were unstable on storage with time, or because the addition of a thickener degraded the cosmetic properties on application to the hair and/or the good compatibility with greasy hair.

The Applicant Company has found that, surprisingly, the use of water-soluble heteropolysaccharides made it possible to thicken the compositions based on the particular surfactants referred to above without losing the advantages of these surfactants. In addition, it has found, in particular, a clear improvement in the foaming properties, particularly as regards the comfort and the softness of the foam, a surprising improvement in detergency and an improvement in the cosmetic properties, particularly as regards the disentangling and the softness of wet and dried hair.

These compositions are, furthermore, readily removed by rinsing with water.

The present invention consequently relates to new cosmetic compositions intended particularly to be applied on hair, containing at least one nonionic, weakly anionic or amphoteric surfactant, such as defined above and at least one water-soluble heteropolysaccharide. These compositions do not contain a strongly anionic surface-active agent nor an oxidizing agent.

The invention also relates to a cosmetic treatment process employing such compositions.

Other subjects will become apparent from reading the description and the examples which follow.

The cosmetic compositions according to the invention are essentially characterised in that they comprise, in a cosmetically acceptable medium:

(a) at least one water-soluble, polyglycerolated, nonionic surface-active agent, chosen preferably from:

(A) the condensation products of a monoalcohol, an α-diol, an alkylphenol or an amide with glycidol or a glycidol precursor, (B) compounds corresponding to the formula:

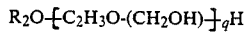

$$R_2O \text{---} [C_2H_3O \text{-}(CH_2OH)]_q H$$

in which $R_2$ denotes an alkyl, alkenyl or alkylaryl radical and q is a statistical value between 1 and 10, these compounds being described more particularly in French Pat. No. 1,477,048, (C) compounds corresponding to the formula:

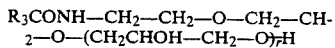

$$R_3CONH\text{---}CH_2\text{---}CH_2\text{---}O\text{---}CH_2\text{---}CH_2\text{---}O\text{---}(CH_2CHOH\text{---}CH_2\text{---}O)_r H$$

in which $R_3$ denotes a radical or a mixture of straight-chain or branched, saturated or unsaturated aliphatic radicals capable of incorporating, if appropriate, one or more hydroxyl groups, containing between 8 and 30 carbon atoms, of natural or synthetic origin, r denotes a integral or decimal number from 1 to 5 and denotes the average degree of condensation, such compounds being described more particularly in French Pat. No. 2,328,763, or (b) a weakly anionic surface-active agent from the polyalkoxycarboxylate group, or (c) an amphoteric surface-active agent chosen from the acylated derivatives of mono- or dicarboxylic diamino acids, optionally in cyclic form, or (d) their mixtures, and at least one water-soluble heteropolysaccharide.

The nonionic surface-active agents of group (A) above correspond, in particular, to the formula:

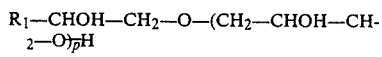

$$R_1\text{---}CHOH\text{---}CH_2\text{---}O\text{---}(CH_2\text{---}CHOH\text{---}CH_2\text{---}O)_p H$$

in which $R_1$ denotes an aliphatic, alicyclic or arylaliphatic radical preferably containing between 7 and 21 carbon atoms, and their mixtures, the aliphatic chains being capable of incorporating ether, thioether or hydroxymethylene groups and in which p is between 1 and 10 inclusive. Such compounds are described particularly in French Pat. No. 2,091,516.

Among the nonionic surfactants defined above, those preferred more particularly correspond to the formula:

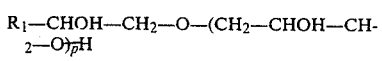

$$R_1\text{---}CHOH\text{---}CH_2\text{---}O\text{---}(CH_2\text{---}CHOH\text{---}CH_2\text{---}O)_p H$$

in which $R_1$ denotes a mixture of alkyl radicals containing between 9 and 12 carbon atoms and p has a statistical value of 3.5, or else $R_1$ denotes a $C_{10}$ alkyl radical and p has a statistical value of 2.5, or $R_2O[C_2H_3O-(CH_2OH)]_qH$ in which $R_2$ denotes the group $C_{12}H_{25}$ and q has a statistical value of 4 to 5, or $R_3-CONH-CH_2-CH_2-O-CH_2C-H_2-O-(CH_2CHOH-CH_2O)_rH$ where $R_3$ denotes a mixture of radicals derived from lauric, myristic, olefic and copra acids and r has a statistical value from 3 to 4.

The surface-active agents from the polyalkoxycarboxylate groups which are particularly preferred are polyglycolic ether carboxylic acids corresponding to the formula:

$R_4-(OCH_2-CH_2)_n-OCH_2-COOH$, whether they are converted into salts or not, where the substituent $R_4$ corresponds to a straight chain containing from 6 to 18 carbon atoms and preferably from 12 to 18 carbon atoms and n is an integer between 5 and 25, preferably between 5 and 10.

Among the compounds belonging to this group, special mention can be made of the product sold at 90% strength of active material under the trade name "Akypo RLM 100" by Chem Y corresponding to the above formula, in which R denotes a mixture of alkyl radicals containing between 12 and 14 carbon atoms and n is equal to 10; the product sold at 90% strength of active material under the trade name "Sandopan DTC Acide" by Sandoz, corresponding to the above formula, in which R denotes a group containing 13 carbon atoms and n is equal to 7, or salts of these compounds; the products sold under the trade name "Sandopan DTC linéaire gel" and "DTC linéaire acide", in which products R denotes a mixture of radicals containing from 12 to 15 carbon atoms and n is equal to 5; the product sold under the trade name "Sandopan KST", in which R denotes an alkyl radical containing 16 carbon atoms and n is equal to 12.

The amphoteric surface-active agents are chosen from those described particularly in the CTFA dictionary, 3rd edition, 1982, and correspond to the following general formulae I and II.

The compounds of formula I correspond to the structure:

$$R_5-CO-NH-CH_2CH_2-N\begin{matrix}CH_2CH_2R_6\\ \\(R_7)_mA^\ominus M^\oplus\end{matrix} \quad (I)$$

in which $R_5$ denotes a straight chain or branched $C_7-C_{17}$ alkyl or alkenyl radical, an alkyl or alkenyl radical derived from a long-chain fatty acid such as that from copra or tallow, $R_6$ denotes an $-OH$, $-OCH_2CH_2COONa$ or $-OCH_2CH_2COOH$ group, $R_7$ denotes $$-CH_2- \text{ or } -CH_2-\underset{OH}{\underset{|}{CH}}-CH_2-,$$

$A^\ominus$ denotes $COO^\ominus$,

M denotes hydrogen or an alkali metal, m denotes 1 or 2.

The compounds of formula II have the structure:

$$R_8-CO-NH-CH_2CH_2-\overset{\oplus}{N}\begin{matrix}CH_2CH_2OH\\-CH_2COO^\ominus\\CH_2COONa\end{matrix} \quad (II)$$

in which $R_8$ denotes a $C_7-C_{17}$ alkyl radical or an alkyl radical derived from copra.

Among the amphoteric surface-active agents which are more particularly preferred, mention may be made of the compound coresponding to the formula:

$$R_5-\underset{O}{\underset{\|}{C}}-NH-CH_2CH_2-N\begin{matrix}CH_2CH_2OCH_2CH_2COONa\\ \\CH_2CH_2COONa\end{matrix}$$

in which $$R_5-\underset{O}{\underset{\|}{C}}-$$

denotes the acyl radical derived from copra; this compound is called "cocoamphocarboxypropionate" in the CTFA dictionary, 3rd edition, 1982, and sold by Miranol under the trade name Miranol C2M SF, and the corresponding acid form and the compound corresponding to the formula:

$$R_8-\underset{O}{\underset{\|}{C}}-NH-CH_2CH_2-\overset{\oplus}{N}\begin{matrix}CH_2CH_2OH\\-CH_2COO^\ominus\\CH_2COONa\end{matrix}$$

in which $$R_8-\underset{O}{\underset{\|}{C}}$$

denotes the acyl radical derived from copra, which corresponds to the trade name of "cocoamphocarboxyglycinate" in the CTFA dictionary, 3rd edition, 1982, and sold by Miranol under the trade name Miranol C2M conc.

The heteropolysaccharides employed in accordance with the invention are synthesised by the fermentation of sugars by microorganisms.

More particularly they may incorporate the xanthane gums produced by the bacteria Xanthomonas Campestri and the mutants or variants of the latter.

The xanthane gums have a viscosity of between 600 and 1,650 cP for an aqueous composition containing 1% of xanthane gum (measured in a Brookfield type LVT viscometer at 60 rev/min) and have a molecular weight of between 1,000,000 and 50,000,000.

The xanthane gums comprise 3 different monosaccharides in their structure, which are mannose, glucose and glucuronic acid in salt form.

Such products are, more particularly: Keltrol marketed by Kelco, a 1% aqueous solution of which has a Brookfield LVT viscosity at 60 rev/minute of 1,200 to 1,600 cP, Kelzan S marketed by Kelco, a 1% aqueous solution of which has a Brookfield LVT viscosity at 60 rev/minute of 850 cP, Rhodopol 23, 23U and 23C, marketed by Rhone-Poulnec, a 0.3% aqueous solution of which has a Brookfield LVT viscosity at 30 rev/minute of 450±50 cP, Rhodigel 23, marketed by Rhone-Poulnec, Deuteron XG marketed by Schöner GmbH, the viscosity of a 1% aqueous solution of which is 1,200 cP, measured in a Brookfield LVT viscometer at 30 rev/minute, Actigum CX9, marketed by Ceca, with a viscosity of 1,200 cP, measured in a Brookfield LVT viscometer at 30 rev/minute on a 1% aqueous solution; Kelzan K9 C57, the viscosity of a 1% aqueous solution of which is 630 to 1,000 cP, measured in a Brookfield LVS viscometer at 60 rev/min, marketed by Kelco, Kelzan K8 B12, the Rotovisco RVI, MVI de Haacke viscosity at 25° C. of which is 1,000 at 10 s$^{-1}$, marketed by Kelco and Kelzan K3 B130, marketed by Kelco.

The heteropolysaccharides may also be chosen from:

(a) the biopolymer PS 87 produced by the bacteria *Bacillus polymyxa* which comprises in its structure glucose, galactose, mannose, fucose and glucuronic acid; this biopolymer PS 87 is described in E.P. Patent Application No. 23,397, (b) the biopolymer S88 produced by the strain Pseudomonas ATCC 31554, which comprises in its structure rhamnose, glucose, mannose and glucuronic acid; this biopolymer is described in the patent G.B. No. 2,058,106, (c) the biopolymer S130, produced by the strain Alcaligenes ATCC 31555, which incorporates in its molecule rhamnose, glucose, mannose and glucuronic acid; this biopolymer is described in the patent G.B. No. 2,058,107, (d) the biopolymer S139 produced by the strain Pseudomonas ATCC 31644, which comprises in its molecule rhamnose, glucose, mannose, galactose and galacturonic acid; this biopolymer is described in U.S. Pat. No. 4,454,316, (e) the biopolymer S198 produced by the strain Alcaligenes ATCC 31853, which comprises in its molecule rhamnose, glucose, mannose and glucuronic acid; this biopolymer is described in E.P. Patent Application No. 64,354, (f) the exocellular biopolymer produced by species of bacteria, yeasts, fungi or algae which are gram-positive or negative; this biopolymer is described in the Patent Application De No. 3,224,547.

The surfactants such as specified above are present in proportions of between approximately 0.5 and 30% and preferably between approximately 1.5 and 15% relative to the total weight of the composition.

The heteropolysaccharide is present in proportions of between approximately 0.1 and 2.5%, preferably between 0.2 and 1.5% by weight.

These compositions have a pH which varies between 3 and 9, and preferably between 4 and 7.

The compositions according to the invention may be empolyed as a shampoo, as hair treatment compositions such as anti-grease or anti-dandruff treatment and more particularly as rinsing compositions to be applied before or after dyeing, before or after bleaching, before or after permanent waving, before or after shampooing or between two stages of a shampoo in order to obtain a hair-conditioning effect.

The cosmetically acceptable medium may consist of water or a water-alcohol mixture and may contain, in addition to the surface-active agents defined above and the heteropolysaccharide, different adjuvants usually employed in cosmetics, such as perfumes, preserving agents, sequestering agents, cationic surface-active agents, cationic polymers, electrolytes, acidifying or alkalizing agents, and the like, with the exception, however, of the combination of a cationic polymer and an anionic polymer, oxidizing agents and strong anionic surfactants. The name strong anionic surfactants is given to surfactants derived from sulphonic, sulphuric, sulphosuccinic, succinic and sarcosinic acids.

The compositions according to the invention, containing a weakly anionic and/or amphoteric surface-active agent, preferably also additionally contain an antigrease or anti-dandruff agent.

When employed for the anti-grease treatment, they may particularly contain the compounds described in French Pat. Nos. 2,000,882, 2,011,940 and 2,133,991, and more particularly S-carboxymethylcysteine, trans-thiolane-3,4-diol S,S-dioxide and oxathiazinone derivatives prepared according to French Pat. No. 2,231,676 and more particularly the potassium salt of 6-methyl-1,2,3-oxathiazine-4-(3H)-one 2,2-dioxide.

When employed as anti-dandruff agents, they may particularly contain zinc or sodium pyridinethiones, bis-(2-pyridyl-1-oxide)disulphide, such as described in French Pat. No. 2,308,624 and its addition products with salts of alkaline earth metals such as, more particularly, the complex of 2,3-dithiopyridine 1,1-dioxide with magnesium sulphate and substituted or unsubstituted 1-hydroxy-2-pyridones such as described in French Pat. No. 2,191,904 and, in particular, the monoethanolamine salt of 1-hydroxy-4-methyl-6-(2,4,4-trimethylpentyl)-2-pyridone.

The cosmetic treatment process according to the invention is essentially characterised in that the composition defined above is applied to hair, and that rinsing is carried out, if necessary, after a few minutes' application.

The treatment may consist:

of washing the hair with the composition described above, followed by a rinse, of an anti-grease or anti-dandruff treatment followed, if appropriate, by a rinse after a few minutes' application, or of a hair-conditioning treatment with the composition according to the invention which is applied before or after dyeing, before or after bleaching, before or after permanent waving, before or after shampooing or between two stages of a shampoo, followed, if appropriate, by a rinse.

The application of these compositions may also be preceded or followed by treatments with lotions containing various components which are active in respect of hair, such as, more particularly, polymers.

The following examples are intended to illustrate the invention without, however, being of a restrictive nature.

EXAMPLE 1

The following composition is prepared:
Polyglocerolated fatty diglycolamide

R—CO—NH—CH$_2$—CH$_2$—O—CH$_2$—CH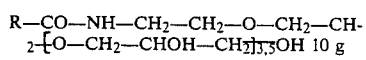
$_2$-[O—CH$_2$—CHOH—CH$_2$]$_{3.5}$OH 10 g R: mixture of radicals derived from C$_{12}$ to C$_{18}$ natural fatty acids
Heteropolysaccharide sold under the trade name of Rhodopol 23C by Rhone-Poulenc 1.0 g
pH adjusted to 5 with lactic acid

EXAMPLE 2

The following composition is prepared:
Nonionic surfactant of formula

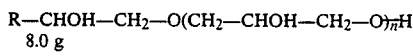
8.0 g

R: mixture of $C_9$-$C_{12}$ alkyl radicals
n denotes an average statistical value of approximately 3.5
Heteropolysaccharide sold under the trade name of Rhodopol 23U by Rhone-Poulenc 1.5 g
pH adjusted to 7 with hydrochloric acid
Water, colorants, stabilizers q.s. 100 g
This composition is employed as a shampoo for washing hair.

EXAMPLE 3

The following composition is prepared:
Nonionic surfactant of formula:

$$RCHOH-CH_2P-[CH_2-CHOH-CH_2O]_{\overline{n}}H$$

R = $C_9$-$C_{12}$-alkyl
n = 3.5 statistical value 10 g
Heteropolysaccharide sold under the trade name of Actigum CX9 by Ceca 1.0 g
pH adjusted to 5 with hydrochloric acid
Colorants, stabilizers q.s.
Water, q.s. 100 g
This composition is employed as a shampoo for washing hair.

EXAMPLE 4

The following composition is prepared:
Nonionic surfactant of formula

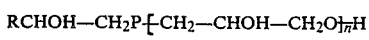

R is a mixture of $C_9$-$C_{12}$ alkyl radicals n denotes an average statistical value of approximately 3.5 8.0 g
Sorbitol monolaurate polyoxyethylenated with 20 moles of EO, sold by Atlas under the trade name Tween 20 5.0 g
Heteropolysaccharide sold under the trade name Keltrol by Kelco 0.5 g
pH adjusted to 8 with triethanolamine
Colorants, stabilizers q.s.
Water, q.s. 100 g
This composition is employed as a shampoo for washing hair.

EXAMPLE 5

The following composition is prepared:
Surfactant of formula

n denotes an average statistical value of 4.2 10 g
Heteropolysaccharide sold under the trade name Rhodopol 23U by Rhone-Poulenc 0.5 g
Stabilizers, perfume q.s.
pH adjusted to 6 with hydrochloric acid
Water, q.s. 100 g
This composition is employed as a shampoo for washing hair.

EXAMPLE 6

The following composition is prepared:
Surfactant of formula:

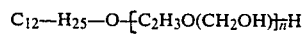

n denotes an average statistical value of approximately 4.2 2.0 g
Heteropolysaccharide sold under the trade name Actigum CX9 by Ceca 1.5 g
Colorant, stabilizers, perfume q.s.
pH adjusted to 5 with hydrochloric acid
Water q.s. 100 g
This composition is applied to wet hair after a shampoo. After a few minutes' application the hair is rinsed with water.

EXAMPLE 7

The following composition is prepared:
Surfactant of formula:

$$CH_3-(CH_2)_{11}-CH_2-(OCH_2CH_2)_7-OCH_2COOH$$

sold in 90% AS strength solution under the trade name "Sandopan DTC Acid" by Sandoz 8.0 g AS
Heteropolysaccharide sold under the trade name "Keltrol" by Kelco 0.5 g AS
Colorants, stabilizers, perfume q.s.
pH adjusted to 6 with hydrochloric acid
Water q.s. 100 g
This composition is employed as a shampoo for washing hair.

EXAMPLE 8

The following composition is prepared:
Polyglycolic ether carboxylic acid of formula:

$$R-(O-CH_2-CH_2)_{10}-OCH_2-COOH$$

in which R = $C_{12}$-$C_{14}$, sold in 90% AS strength under the trade name "Akypo.RLM.100" by Chem.Y. 1.5 g AS
Heteropolysaccharide sold under the trade name "Keltrol" by Kelco 0.8 g AS
Colorant, stabilizer, perfume q.s. pH adjusted to 5 with hydrochloric acid
Water q.s. 100 g
When applied on wet hair after a shampoo, this composition spreads very well. After a few minutes' application, the hair is rinsed with water.

EXAMPLE 9

The following composition is prepared:
38% strength AS amphoteric derivative sold under the trade name Miranol C2M conc. by Miranol 15.0 g AS
Heteropolysaccharide sold under the trade name of Keltrol by Kelco 1.0 g AS
pH adjusted to 4 with hydrochloric acid
Colorants, stabilizers, water q.s. 100 g
This composition is in the form of a thickened liquid which is employed as a shampoo.
Hair washed with this shampoo is shiny, soft to the touch and disentangles readily.

EXAMPLE 10

The following composition is prepared:
Heteropolysaccharide sold under the trade name of Rhodopol 23U by Rhone-Poulnec 0.8 g
38% strength AS amphoteric derivative sold under the trade name Moranol C2M conc. by Moranol 2.0 g AS
Potassium salt of 6-methyl-1,2,3-oxathiazin-4-(3H)-one 2,2-dioxide, sold by Hoechst under the trade name Acesulfam K 3.0 g
pH adjusted to 7 with hydrochloric acid
Stabilizers, perfumes, water q.s. 100 g This composition is employed as a ringing composition or "rinse" for the treatment of greasy hair.

EXAMPLE 11

The following composition is prepared:
Heteropolysaccharide sold under the trade name of Rhodopol 23U by Rhone-Poulnec 1.0 g
38% strength AS amphoteric derivative sold under the trade name Miranol C2M con. by Miranol 2.0 g
zinc pyridinethione sold by Olin 0.8 g
pH adjusted to 6.7 with hydrochloric acid
Stabilizers, perfumes, water q.s. 100 g This composition is employed as a rinsing composition or "rinse" for the anti-dandruff treatment.

EXAMPLE 12

The following composition is prepared:
Nonionic surfactant of formula:

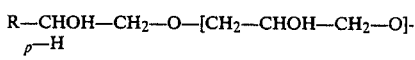
R—CHOH—CH$_2$—O—[CH$_2$—CHOH—CH$_2$—O]$_p$—H where R is a decyl radical and p denotes an average statistical value of 2.5  0.5 g AS
Condensate of epichlorohydrin with a condensate of adipic acid and diethylenetriamine, prepared according to Example 1a of French Pat. No. 2,252,840 0.5 g AS
Heteropolysaccharide sold under the trade name of Rhodigel 23 by Rhone-Poulnec 2.0 g AS
Distearyldimethylammonium chloride 0.3 g AS
Colorants, stabilizers, perfume q.s.
pH adjusted to 8 with hydrochloric acid
Water q.s. 100 g This composition is applied to wet hair after a shampoo. After a few minutes' application the hair is rinsed with water.

EXAMPLE 13

The following composition is prepared:
Nonionic surfactant of formula:

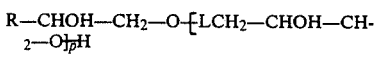
R—CHOH—CH$_2$—O—[LCH$_2$—CHOH—CH$_2$—O]$_p$H where R is a decyl radical and p denotes an average statistical value of 2.5 10.0 g AS
Heteropolysaccharide sold under the trade name of Kelzan S by Kelco 0.9 g AS
pH adjusted to 6.5 with hydrochloric acid
Colorants, stabilizers, perfume q.s.
Water q.s. 100 g This composition, which has a soft and agreeable foam is used for washing hair.

EXAMPLE 14

A shampoo with the following composition is prepared:
Heteropolysaccharide sold under the trade name of Actigum CX 9 by Ceca 0.5 g AS
Amphoteric derivative sold under the trade name of Miranol C2M SF by Miranol 10.0 g AS
Colorants, stabilizers, perfume q.s.
pH adjusted to 7 with hydrochloric acid
Water q.s. 100 g This composition is used for washing hair and makes it soft and shiny.

EXAMPLE 15

The following anti-dandruff composition is prepared:
Heteropolysaccharide sold under the trade name of Kelzan S by Kelco 1.0 g
Amphoteric derivative sold under the trade name of Miranol C2M SF by Miranol 2.0 g AS
Monoethanolamine salt of 1-hydroxy-4-methyl-6-(2,4,4-trimethylpentyl)-2-pyridone, sold under the trade name Octoptrox by Hoechst 1.0 g AS
Colorants, stabilizers, perfume q.s.
pH adjusted to 8 with hydrochloric acid
Water q.s. 100 g This composition is applied to wet hair at the scalp skin and after a shampoo. After a few minutes' application, the hair is rinsed with water.

EXAMPLE 16

The following composition is prepared:
Heteropolysaccharide sold under the trade name of Rhodopol 23U by Rhone-Poulnec 1.5 g
Trideceth-7-carboxylic acid of formula

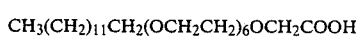
$CH_3(CH_2)_{11}CH_2(OCH_2CH_2)_6OCH_2COOH$ sold at 90% strength AS by Sandoz under the trade name Sandopan DTC Acide neutralized with sodium hydroxide 12.0 g AS
Colorants, stabilizers, perfume q.s.
pH adjusted to 6 with sodium hydroxide
Water q.s. 100 g This composition is employed as a shampoo for washing hair.

EXAMPLE 17

The following composition is prepared:
Heteropolysaccharide sold under the trade name of Actigum CX 9 by Ceca 0.8 g
Sodium salt of trideceth-7-carboxylic acid, of formula

$CH_3(CH_2)_{11}CH_2-(OCH_2CH_2)_6OCH_2COONa$ sold at 70% strength AS under the trade name Sandopan DTC Linéaire Gel by Sandoz 1.0 g AS
Potassium salt of 6-methyl-1,2,3-oxathiazine-4-(3H)one 2,2-dioxide, sold under the trade name of Acesulfam K by Hoechst 0.5 g
Colorants, stabilizers, perfume q.s.
pH adjusted to 4.5 with hydrochloric acid
Water q.s. 100 g This composition is employed as a rinsing composition after a shampoo for the treatment of greasy hair.

EXAMPLE 18

An anti-dandruff after-shampoo of the following composition is prepared:

Heteropolysaccharide sold under the trade name Kelzan K9 C 57 by Kelco 1.2 g
Sodium salt of trideceth-7-carboxylic acid, of formula $$CH_3-(CH_2)_{11}-CH_2-(O-CH_2CH_2)_6-OCH_2-COONa$$

sold at 70% strength AS under the trade name of Sandopan DTC Linéaire Sel by Sandoz 1.0 g AS
Monoethanolamine salt of 1-hydroxy-4-methyl-6-(2,4,4-trimethylpentyl)-2-pyridone, sold under the trade name Octopirox by Hoechst 1.0 g AS
Colorants, stabilizers, perfumes q.s.
pH adjusted to 7 with hydrochloric acid
Water q.s. 100 g

What is claimed is:

1. A hair cosmetic composition comprising in a cosmetically acceptable medium is water or a water alcohol mixture at least one surfactant selected from the group consisting of
   (a) a water-soluble polyglycerolated nonionic surface active agent,
   (b) a weakly anionic polyalkoxycarboxylate surface active agent,
   (c) an amphoteric surface active agent selected from the group consisting of an acylated derivative of a mono- or dicarboxylic diamino acid and an acylated derivative of a cyclic mono- or dicarboxylic diamino acid and
   (d) mixtures thereof, and at least one water soluble heteropolysaccharide synthesized by the fermentation of sugars by microorganisms, said surfactant being present in an amount ranging from about 0.5 to 30 percent by weight and said water soluble heteropolysaccharide being present in an amount ranging from about 0.1 to 2.5 percent by weight.

2. The composition of claim 1 wherein said nonionic surface active agent is selected from the group consisting of
   (A) the condensation product of a monoalcohol, an α-diol, an alkylphenol or an amide with glycidol or a glycidol precursor,
   (B) a compound having the formula $$R_2O \text{-}\!\!\left[C_2H_3O\text{-}(CH_2OH)\right]_{\overline{q}}\!H$$

wherein
   $R_2$ represents alkyl, alkenyl or alkylaryl and q has a statistical value between 1 and 10 inclusive,
   (C) a compound having the formula $$R_3CONH-CH_2-CH_2-O-CH_2-CH_2-O-(CH_2CHOH-CH_2-O)_{\overline{r}}E$$

wherein
   $R_3$ represents a radical or mixture of straight chain or branched, saturated or unsaturated aliphatic radicals containing between 8 and 30 carbon atoms of natural or synthetic origin, or an aliphatic radical containing between 8 and 30 carbon atoms and one or more hydroxyl groups of natural or synthetic origin and
   r represents a number from 1 to 5 and denotes the average degree of condensation.

3. The composition of claim 1 wherein said composition includes at least one adjuvant selected from the group consisting of perfume, a preserving agent, a sequestering agent, a cationic surface active agent, a cationic polymer and an electrolyte.

4. A composition comprising in water or a water-alcohol medium at least one of a surfactant selected from the group consisting of
   (a) a water-soluble polyglycerolated nonionic surface active agent comprising
      (i) a condensation product of a monoalcohol, an α-diol, an alkylphenol or an amide with glycidol or a glycidol precursor,
      (ii) a compound having the formula $$R_2O\text{-}\!\!\left[C_2H_3O\text{-}(CH_2OH)\right]_{\overline{q}}\!H$$

wherein
      $R_2$ represents alkyl, alkenyl or alkylaryl and q is a statistical value between 1 and 10, or
      (iii) a compound having the formula $$R_3CONH-CH_2-CH_2-O-CH_2-CH_2-O-(CH_2CHOH-CH_2-O)_{\overline{r}}H$$

wherein
      $R_3$ represents a radical or mixture of straight chain or branched, saturated or unsaturated aliphatic radicals containing from 8 to 30 carbon atoms, or an aliphatic radical containing from 8 to 30 carbon atoms and at least one hydroxyl group, or
   (b) weakly anionic surface active agent having the formula $$R_4-(OCH_2-CH_2)_n-OCH_2-COOH$$

wherein
   $R_4$ represents a straight chain containing from 6 to 18 carbon atoms and
   n is an integer ranging from 5 to 25, or
   (c) an amphoteric surface active agent having the formula

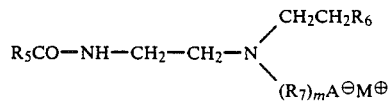

wherein
   $R_5$ represents a straight chain or branched alkyl or alkenyl radical containing 7 to 17 carbon atoms, or an alkyl or alkenyl radical derived from a long-chain fatty acid,
   $R_6$ represents $-OH$, $-OCH_2CH_2COONa$ or $-OCH_2CH_2COOH$,
   $R_7$ represents $$-CH_2- \text{ or } -CH_2-\underset{OH}{CH}-CH_2-$$

$A^{\ominus}$ represents $COO^{63}$,
   M represents hydrogen or an alkali metal and
   m represents 1 or 2,
   (d) a mixture of two or more of (a), (b) and (c) defined above, and at least one water soluble heteropolysaccharide selected from the group consisting of
  (1) a xanthane gum having a molecular weight between 1,000,000 and 50,000,000,
  (2) bipolymer PS 87 produced by the bacteria *Bacillus polymyxa* and comprising glucose, galactose, mannose, fucose and glucuronic acid in its structure,
  (3) bipolymer S 88 produced by the strain Pseudomonas ATCC 31554 and comprising rhamnose, glucose, mannose and glucuronic acid in its structure,
  (4) bipolymer S 130 produced by the strain Alcaligenes ATCC 31555 and comprising rhamnose, glucose, mannose and glucuronic acid in its structure,
  (5) bipolymer S 139 produced by the strain Pseudomonas ATCC 31644 and comprising rhamnose, glucose, mannose, galactose and galacturonic acid in its structure,
  (6) bipolymer S 198 produced by the strain Alcaligenes ATCC 31853 and comprising rhamnose, glucose, mannose and glucuronic acid in its structure, and
  (7) exocellular bipolymer produced by species of bacteria, yeasts, fungi or algae which are gram-positive or negative,
said surfactant being present in an amount ranging from about 0.5 to 30 weight percent based on the total weight of said composition and
said water soluble heteropolysaccharide being present in an amount ranging from about 0.1 to 2.5 weight percent based on the total weight of said composition.

5. A composition according to claim 1, wherein the water-soluble heteropolysaccharide is selected from the group consisting of: xanthane gums having a molecular weight of between 1,000,000 and 50,000,000 and the following biopolymers: biopolymer PS 87 produced by the bacterium *Bacillus polymyxa*, which comprises glucose, galactose, mannose, fucose and glucuronic acid in its structure; biopolymers S88, produced by the strain Pseudomonas ATCC 31554, S130, produced by the strain Alcaligenes ATCC 31555, and S198, produced by the strain Alcaligenes ATCC 31853, comprising rhamnose, glucose, mannose and glucuronic acid in their molecules; biopolymer S139, produced by the strain Pseudomonas ATCC 31644 comprising rhamnose, glucose, mannose, galactose and galacturonic acid in its molecules; and the exocellular biopolymer produced by the species of bacteria, yeasts, fungi or algae which are gram-positive or negative.

6. A composition according to claim 1, wherein the nonionic surface agent is a compound corresponding to the formula:

$$R_1-CHOH-CH_2-O-(CH_2-CHOH-CH_2-O)_pH$$

in which $R_1$ denotes an aliphatic, alicyclic or arylaliphatic radical containing between 7 and 21 carbon atoms and their mixtures, the aliphatic chains being capable of incorporating ether, thioether or hydroxymethylene groups and where p is between 1 and 10 inclusive.

7. A composition according to any one of claims 1, wherein the nonionic surface-active agent is a compound corresponding to the formula:

$$R_1-CHOH-CH_2-O-(CH_2-CHOH-CH_2-O)_pH$$

where $R_1$ denotes a mixture of alkyl radicals containing between 9 and 12 carbon atoms and p has a statistical value of approximately 3.5, or else $R_1$ denotes a decyl radical and p has a statistical value of 2.5.

8. A composition according to claim 1, wherein the nonionic surface agent is a compound corresponding to the formula:

$$R_2O-C_2H_3O-(CH_2OH)]_qH$$

in which $R_2$ denotes a $C_{12}H_{25}$ group and q has a statistical value of 4 to 5.

9. A composition according to claim 1, wherein the nonionic surface agent corresponds to the formula:

$$R_3-CONH-CH_2-CH_2-O-CH_2-CH_2-O-(CH_2CHOH-CH_2O)_rH$$

where $R_3$ denotes a mixture of radicals derived from lauric, myristic, oleic and copra acids and r has a statistical value from 3 to 4.

10. A composition according to claim 1, wherein
  the polyalkoxycarboxylate is a carboxylic acid of a polyglycolic ether corresponding to the formula:

$$R_4-(OCH_2-CH_2)_n-OCH_2-COOH$$

whether converted to a salt or not, where the substituent $R_4$ corresponds to a straight chain containing from 6 to 18 carbon atoms and n is an integer between 5 and 25.

11. A composition according to claim 10, wherein $R_4$ is an alkyl group containing 12 to 18 carbon atoms and n is an integer between 5 and 10.

12. A composition according to claim 1, wherein the weakly anionic surface-active agent corresponds to the formula:

$$R_4-(OCH_2-CH_2)_n-OCH_2-COOH$$

in which:
  (a) $R_4$ denotes a mixture of alkyl radicals containing between 12 and 14 carbon atoms and n is equal to 10; or
  (b) $R_4$ denotes a group containing 13 carbon atoms and n is equal to 7; or
  (c) $R_4$ denotes a mixture of alkyl radicals containing from 12 to 15 carbon atoms and n is equal to 5;
  (d) $R_4$ denotes an alkyl radical containing 16 carbon atoms and n is equal to 12.

13. A composition according to claim 1, wherein the amphoteric surfactant corresponds to the formulae:

$$R_5-CO-NH-CH_2CH_2-N\begin{matrix}CH_2CH_2R_6\\ \\(R_7)_mA^\ominus M^\oplus\end{matrix} \quad (I)$$

in which
  $R_5$ denotes a $C_7$-$C_{17}$ straight-chain or branched alkyl or alkenyl radical, an alkyl or alkenyl radical derived from long-chain fatty acids,
  $R_6$ denotes an OH, OCH$_2$CH$_2$COONa or OCH$_2$CH$_2$COOH group;
  $R_7$ denotes —CH$_2$—;

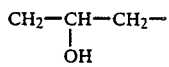

A⊖ denotes a COO⊖ group
M denotes H or an alkali metal;
m denotes 1 or 2 or

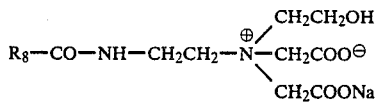 (II)

in which $R_8$ denotes an alkyl group containing 7 to 17 carbon atoms or an alkyl group derived from copra.

14. A composition according to claim 13, wherein in the compound corresponding to formula I the alkyl radical derived from long-chain fatty acids is chosen from radicals derived from copra and tallow.

15. A composition according to claim 13, wherein the amphoteric surface-active agent is a compound of formula:

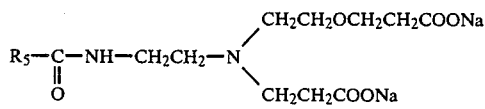

in which

denotes the acyl radical derived from copra.

16. A composition according to claim 13, wherein the amphoteric surface-active agent corresponds to the formula:

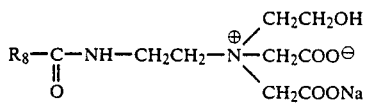

in which

denotes the acyl radical derived from copra.

17. A composition according to claim 5, wherein the xanthane gum has a viscosity of between 600 and 1,650 cP for an aqueous composition containing 1% of xanthane gum, measured in a Brookfield type LVT viscometer at 60 rev/min.

18. A composition according to claim 1, wherein the surface-active agent is present in a proportion of approximately 0.5 to 30% by weight.

19. A composition according to claim 1, having pH between 3 and 9.

20. A composition according to claim 1, containing in addition an anti-grease or anti-dandruff agent.

21. A hair treatment process which comprises applying at least one composition such as specified in claim 1 on hair.

22. A hair washing process which comprises applying on hair at least one composition such as specified in claim 1 followed by rinsing.

23. An anti-grease or anti-dandruff hair treatment process wherein at least one composition such as specified in claim 20 is applied to hair and that after a few minutes' application the hair is rinsed if appropriate.

24. A hair conditioning process wherein at least one composition such as specified in claim 1 is applied, before or after colouring, before or after bleaching, before or after permanent waving, before or after shampooing or between two stages of a shampoo.

* * * * *